United States Patent [19]

Davis et al.

[11] 4,297,496

[45] Oct. 27, 1981

[54] NITRIMINE DERIVATIVES

[75] Inventors: Royston H. Davis, Sittingbourne; John H. Davies, Canterbury, both of England

[73] Assignee: Shell Oil Company, Houston, Tex.

[21] Appl. No.: 162,340

[22] Filed: Jun. 23, 1980

[30] Foreign Application Priority Data

Jul. 30, 1979 [GB] United Kingdom ............... 26479/79

[51] Int. Cl.³ ............................................. C07D 239/18
[52] U.S. Cl. ..................................... 544/332; 424/251
[58] Field of Search ......................................... 544/332

[56] References Cited

U.S. PATENT DOCUMENTS 3,969,354 7/1976 Tieman et al. ...................... 544/335

OTHER PUBLICATIONS

The Chemistry of Heterocyclic Compounds, The Pyrimidines, Brown, p. 342, pub. by Interscience (1962).

Primary Examiner—Paul M. Coughlan, Jr.

[57] ABSTRACT

A 2-nitriamino-1,3-diazacyclohexane of the formula

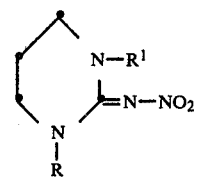

wherein R is hydrogen, alkyl of from one to six carbon atoms or alkanoyl of from one to seven carbon atoms, and $R^1$ is hydrogen or alkyl of from one to six carbon atoms, useful as insecticides.

4 Claims, No Drawings

NITRIMINE DERIVATIVES

DESCRIPTION OF THE INVENTION

It has been discovered that useful insecticidal properties are possessed by heterocyclic derivatives of nitrimine, which derivatives are described by the formula:

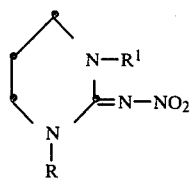

wherein R is hydrogen, alkyl of from one to six carbon atoms or alkanoyl of from one to seven carbon atoms, and $R^1$ is hydrogen or alkyl of from one to six carbon atoms.

In these derivatives, those wherein R is hydrogen or $R^1$ is hydrogen exist as tautomers; these tautomers are included in and are represented by Formula I.

Each alkyl moiety, including that of the alkanoyl moiety, suitably contains from one to six carbon atoms and may be straight-chain or branched-chain in configuration.

The compounds of the invention can be prepared by
(a) effecting reaction of a compound of the formula

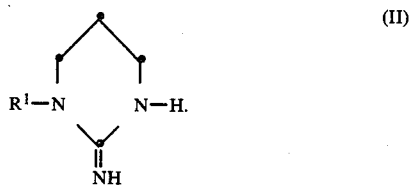

or a tautomer thereof, where $R^1$ is hydrogen, alkyl or alkylcarbonyl, or an acid-addition salt thereof, with nitric acid; or (b) reacting nitroguanidine with a compound of the formula

where $R^1$ is as defined above; optionally followed when $R^1$ is hydrogen by acylation to give a compound of formula I where R is alkylcarbonyl.

Reaction (a) may conveniently be effected in acid conditions, e.g. in the presence of concentrated sulfuric acid, and at reduced temperature, e.g. 0° to 5° C.

Reaction (b) may conveniently be effected in aqueous solution at elevated temperature, e.g. 50° to 100° C., preferably about 70° C.

The optional acylation step when $R^1$ is hydrogen may conveniently be effected by reaction with the appropriate acyl halide, especially the acyl chloride, or acyl anhydride in an inert solvent, e.g. chloroform, at elevated temperature, e.g. reflux temperature of the reaction mixture.

The compounds of formula II or their tautomers are either known compounds (see, for example, Schöberl and Magosch, Ann., 742, 74, (1970); Kwok and Pranc, J. Org. Chem., 32, 738, (1967); Moriconi and Levasco, J. Org. Chem., 33, 2109, (1968); UK Patent Specification No. 765,457) or are readily prepared by known methods from known starting materials as will be readily appreciated by those skilled in the art. Similarly, the compounds of formula III are either known compounds or are readily prepared by known methods from known starting materials.

The compounds of the invention have exhibited pesticidal, e.g. insecticidal and acaricidal, activity. The invention therefore provides a pesticidal composition which comprises as active ingredient a compound of the general formula I, in association with an inert carrier. The invention also provides a method of combating pests at a locus, which comprises applying to that locus a compound of the general formula I or a pesticidal composition according to the invention.

A carrier in a composition of the invention may be a solid or a liquid, including a material which is normally gaseous but which has been compressed to form a liquid, inorganic or organic, and of synthetic or natural origin. The active ingredient is suitably formulated with at least one carrier to facilitate its application to the locus, for example, plants, seeds or soil, to be treated, or to facilitate storage, transport or handling.

Preferably, a composition of the invention contains at least two carriers, at least one of which is a surface-active agent. The surface-active agent may be an emulsifier, a dispersing agent or a wetting agent, it may be non-ionic or ionic. Pesticidal compositions are generally formulated and transported in a concentrated form which is subsequently diluted by the farmer or other user before application. A surface-active agent facilitates this process of dilution.

Any of the carriers commonly used in the formulation of pesticides may be used in the compositions of the invention, and suitable examples of these are to be found, for example, in British Patent Specification No. 1,232,930.

The composition of the invention may, for example, be formulated as a wettable powder, microcapsules, a dust, granules, a solution, an emulsifiable concentrate, an emulsion, a suspension concentrate or an aerosol. The composition may have controlled release properties, or may be suitable for use as a bait.

Wettable powders usually contain 25, 50 or 75%w of active ingredient and may contain, in addition to inert solid material, 3–10%w of a dispersing agent and, where necessary, 0–10%w of a stabilizer, a penetrant and/or a sticker. A dust is usually formulated as a dust concentrate having a composition similar to that of a wettable powder but without a dispersant, and is diluted in the field with further solid carrier to give a composition usually containing 0.05–10% of active ingredient. Granules usually have a size in the range of from 10 to 100 BS mesh (1.676–0.152 mm) and may be manufactured by agglomeration or impregnation techniques. Generally, granules will contain 0.05–25%w active ingredient and 0–10%w of additives, for example, a stabilizer, slow release modifier and/or a binding agent.

Emulsifiable concentrates usually contain, in addition to a solvent, and, when necessary, co-solvent, 10–50% w/v active ingredient, 2–20% w/v emulsifier and 0–20% w/v of other additives, for example, a stabilizer, a penetrant and/or a corrosion inhibitor. A suspension concentrate is a stable, non-sedimenting, flowable product and usually contains 10–75%w active ingredient, 0.5–15%w of dispersing agent, 0.1–10%w of suspending agent, for example, protective colloid and/or a thixotropic agent, and 0–10%w of other additives including, for example, a defoamer, a corrosion inhibitor, a stabilizer, a penetrant and/or a sticker, and as dispersant, water or an organic liquid in which the active ingredient is substantially insoluble; certain organic additives and/or inorganic salts may be dissolved in the dispersant to assist in preventing sedimentation or as anti-freeze for water.

The aqueous dispersions and emulsions formed by diluting a wettable powder or an emulsifiable concentrate of the invention with water, also lie within the scope of the present invention. Such dispersions and emulsions may be of the water-in-oil or of the oil-in-water type, and may have a thick "mayonnaise"-like consistency.

A composition of the invention may also contain other ingredients, for example, one or more other compounds possessing pesticidal, herbicidal or fungicidal properties, or attractants, for example, pheromones or food ingredients, for use in baits and trap formulations.

The compounds of the invention have low mammalian toxicity.

The invention is illustrated in the following examples thereof. In each case, the identity of the product was confirmed by appropriate chemical and spectral analyses.

EXAMPLE 1

3-Methyl-2-nitrimino-1,3-diazacyclohexane (1)

5.65 g of 3-methyl-2-amino-1,3-diazacyclohexane was added slowly and with stirring to 15 ml of 98% sulfuric acid at 5° C. The resulting solution was cooled to 0° C. and 2.5 ml of fuming nitric acid was added drop-by-drop. After stirring for 45 minutes at 5° C., the mixture was poured onto 100 g of crushed ice. Extraction with chloroform followed by evaporation of the chloroform from the extract yielded a white solid which was recrystallized from isopropanol to give 1, as a solid, m.p.: 104°–105° C.

EXAMPLE 2

1-Acetyl-3-methyl-2-nitrimino-1,3-diazacyclohexane (2)

A solution of 1 g of 3-methyl-2-nitrimino-1,3-diazacyclohexane and 1.5 g of acetyl chloride in 15 ml of chloroform was refluxed for 8 hours. The solvent in the reaction mixture was removed under vacuum and the residue was purified by chromatography on a silica gel column using chloroform as eluent to give 2, as a solid, m.p.: 103°–104° C.

Pesticidal Tests

The insecticidal and miticidal activity of the compounds of the present invention was assessed employing the following pests:
Insects:
  *Musca domestica* (M.d.)
  *Spodoptera littoralis* (S.l.)
  *Megoura viciae* (M.v.)
  *Heliothis zea* (H.z.)
Mites:
  *Tetranychus urticae* (T.u.)
The test methods employed for each species were:
(i) *Musca domestica* (M.d.)

A 0.4% by weight solution in acetone of the compound to be tested was prepared and taken up in a micrometer syringe. Two- to three-day-old adult female houseflies (*Musca domestica*) were anesthetized with carbon dioxide, and 1 μl of the test solution was applied to the ventral side of the abdomen of each fly, 20 flies being treated. The treated flies were held in glass jars covered with paper tissues held by an elastic band. Cotton-wool pads soaked in dilute sugar solution were placed on top of the tissue as food. After 24 hours the percentage of dead and moribund flies was recorded.

(ii) *Spodoptera littoralis* (S.l.)

Pairs of leaves were removed from broad bean plants and placed on filter paper inside plastic petri dishes. The leaves were sprayed on the undersurface with an aqueous formulation containing 20% by weight of acetone, 0.05% by weight of TRITON X-100 (Trademark) as wetting agent and 0.4% by weight of the compound to be tested. Varying concentrations were obtained by diluting the formulation. After spraying, the leaves were left to a ½–1 hour drying period and then each leaf pair was infested with ten larvae of the Egyptian cotton leafworm (*Spodoptera littoralis*). After 24 hours the percentage of dead and moribund larvae was recorded.

(iii) *Megoura viciae* (M.v.)

Tests were carried out on adult vetch aphids (*Megoura viciae*) by similar methods to that used for *Spodoptera littoralis* in (ii) above.

(iv) *Heliothis zea* (H.z.)

The compounds to be tested were incorporated in aqueous solutions containing 20% by weight of acetone, 0.04% by weight of Atlox 1045A (Trademark) and 0.2% by weight of the test compound, more dilute solutions for dosage-mortality curves being made by diluting the 0.2% solution with an aqueous solution of 0.05% by weight of Atlox 1045A. Cut Windsor broad bean plants were placed on a turntable and sprayed with 4 ml of test solution. Immediately after spraying, 5 corn earworm larvae (*Heliothis zea*) were transferred to each plant which was inserted into water through a hole in a test board and the environment was maintained at a temperature of 27° C. and 40–50% relative humidity. Mortality was assessed after 44 to 46 hours.

(v) *Tetranychus urticae* (T.u.)

Discs were cut from the leaves of French bean plants and were placed on filter paper kept moist by a cotton-wool wick dipping into water. Each disc was infested with ten adult mites, and the discs were then sprayed with a solution or suspension of the test compound in acetonewater (20:80) containing 0.05% of TRITON X-100 (Trademark) as wetting agent. After 24 hours the percentage of dead and moribund mites was assessed.

The results are shown in Table I, in which the test species are identified by the initials noted above. For *Musca domestica, Spodoptera littoralis, Megoura viciae* and *Tetranychus urticae,* the activity of the compound is expressed in terms of its Toxicity Grade according to the following scheme:

| $LC_{50}$ of: | Toxicity Grade |
| --- | --- |
| >0.6% compound in test solution | 0 |
| ≦0.6% and >0.2% compound in test solution | 1 |
| ≦0.2% and >0.06% compound in test solution | 2 |
| ≦0.06% and >0.02% compound in test solution | 3 |
| ≦0.02% compound in test solution | 4 |

For *Heliothis zea,* the activity of the compound is expressed in the form of its Toxicity Index (T.I.) which is calculated from the following equation:

Toxicity Index $(T.I.) = \dfrac{LC_{50} \text{ of ethyl parathion (standard)}}{LC_{50} \text{ of test compound}}$

TABLE I

| Compound No. | Toxicity Grade | | | | Toxicity Index Hz |
| --- | --- | --- | --- | --- | --- |
| | M.d. | S.l. | M.v. | T.u. | |
| 1 | 2 | 3 | 2 | 1 | 141 |
| 2 | 2 | 3 | 2 | 1 | |

We claim:

1. A nitriminoheterocyclic compound of the general formula:

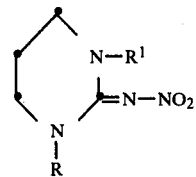

wherein R is hydrogen, alkyl of from one to six carbon atoms or alkanoyl of up to seven carbon atoms, and $R^1$ is hydrogen or alkyl of from one to six carbon atoms.

2. A compound according to claim 1 wherein R is hydrogen or acetyl and $R^1$ is methyl.

3. 3-Methyl-2-nitrimino-1,3-diazacyclohexane.

4. 1-Acetyl-3-methyl-2-nitrimino-1,3-diazacyclohexane.

* * * * *